United States Patent
Etou et al.

(10) Patent No.: US 11,225,446 B2
(45) Date of Patent: Jan. 18, 2022

(54) METHOD FOR PRODUCING PERFLUOROALKADIENE COMPOUNDS

(71) Applicant: DAIKIN INDUSTRIES, LTD., Osaka (JP)

(72) Inventors: Yuusuke Etou, Osaka (JP); Atsushi Maruo, Osaka (JP); Katsuya Nakai, Osaka (JP); Kazuhiro Takahashi, Osaka (JP)

(73) Assignee: DAIKIN INDUSTRIES, LTD., Osaka (JP)

( * ) Notice: Subject to any disclaimer, the term of this patent is extended or adjusted under 35 U.S.C. 154(b) by 0 days.

(21) Appl. No.: 17/225,598

(22) Filed: Apr. 8, 2021

(65) Prior Publication Data
US 2021/0221757 A1    Jul. 22, 2021

Related U.S. Application Data

(62) Division of application No. 16/482,856, filed as application No. PCT/JP2018/003556 on Feb. 2, 2018, now Pat. No. 11,001,545.

(30) Foreign Application Priority Data

Feb. 3, 2017 (JP) .................. 2017-018793
Oct. 23, 2017 (JP) .................. 2017-204360

(51) Int. Cl.
*C07C 17/25* (2006.01)
*C07C 21/19* (2006.01)
*C08F 36/16* (2006.01)
*C09K 13/00* (2006.01)

(52) U.S. Cl.
CPC .............. *C07C 17/25* (2013.01); *C07C 21/19* (2013.01); *C09K 13/00* (2013.01); *C08F 36/16* (2013.01)

(58) Field of Classification Search
CPC ......... C07C 17/25; C07C 21/19; C07C 21/20; C09K 13/00; C08F 36/16
See application file for complete search history.

(56) References Cited

U.S. PATENT DOCUMENTS

| | | | |
|---|---|---|---|
| 4,654,448 | A | 3/1987 | Bargigia et al. |
| 6,610,896 | B2 | 8/2003 | Miki |
| 2002/0193643 | A1 | 12/2002 | Miki et al. |
| 2008/0262195 | A1 | 10/2008 | Ji et al. |

FOREIGN PATENT DOCUMENTS

| | | |
|---|---|---|
| JP | 62-26240 | 2/1987 |
| JP | 2000-355699 | 12/2000 |
| JP | 2001-192345 | 7/2001 |
| JP | 2001-192347 | 7/2001 |
| JP | 2009-258351 | 11/2009 |
| TW | 200842121 | 11/2008 |

OTHER PUBLICATIONS

International Search Report dated Mar. 20, 2018 in International (PCT) Application No. PCT/JP2018/003556.
Lo, "Reaction of Perfluoroalkyl Halides with Grignard Reagents", Journal of Organic Chemistry, 1971, vol. 36, No. 2, pp. 364-366.
Extended European Search Report dated Nov. 30, 2020 in corresponding European Patent Application No. 18747524.9.

*Primary Examiner* — Jafar F Parsa
(74) *Attorney, Agent, or Firm* — Wenderoth, Lind & Ponack, L.L P.

(57) ABSTRACT

According to a method for producing a perfluoroalkadiene compound represented by general formula (1): $CF_2=CF-(CF_2)_{n-4}-CF=CF_2$ (1), wherein n is an integer of 4 or more, the method comprising a reaction step of adding a nitrogen-containing compound to a solution of a compound represented by general formula (2): $X^1CF_2-CFX^2-(CF_2)_{n-4}-CF_2-CF_2X^1$ (2), wherein n is the same as above, $X^1$ is the same or different and is a halogen atom other than fluorine, and $X^2$ is a halogen atom, the perfluoroalkadiene compound can be obtained at a high yield.

8 Claims, No Drawings

METHOD FOR PRODUCING PERFLUOROALKADIENE COMPOUNDS

TECHNICAL FIELD

The present invention relates to a method for producing a perfluoroalkadiene compound.

BACKGROUND ART

Perfluoroalkadiene compounds are useful as dry etching gases for semiconductors, as well as useful as refrigerants, foaming agents, heat transfer media, etc.; and have two double bonds between carbon atoms. In particular, hexafluorobutadiene having four carbon atoms, and a double bond at both terminals, is used for various purposes.

As a method for producing a perfluoroalkadiene compound, a method for carrying out deiodofluorination of α,ω,-diiodo pentafluoroalkane by a reaction of an organic metal compound such as Mg, Zn, Cd, or Li at a desired temperature in the presence of a polar aprotic solvent that belongs to ethers and cyclic ethers (see, for example, Patent Literature 1) is known. Additionally, performing deiodofluorination of a compound such as $ICF_2CF_2CF_2CF_2I$ in the presence of metal zinc and a nitrogen-containing compound is also known as a method for producing a perfluoroalkadiene compound.

CITATION LIST

Patent Literature

PTL 1: JP1987-26240A

SUMMARY OF INVENTION

Technical Problem

However, the organic metal reagents (n-butyl lithium, ethylmagnesium bromide, etc.) used in the method of PTL 1 are expensive, are difficult to handle due to their high reactivity, and cannot provide sufficient yield. Further, even in the method for performing deiodofluorination of a compound such as $ICF_2CF_2CF_2CF_2I$ in the presence of metal zinc and a nitrogen-containing compound, the yield is still insufficient.

The present invention solves the above problems, and aims to provide a method for obtaining a perfluoroalkadiene compound at a high yield.

Solution to Problem

The present inventors conducted extensive research to solve the above problems. As a result, they found that a perfluoroalkadiene compound can be obtained at a high yield by adding a nitrogen-containing compound and optionally zinc to a solution of a specific compound. The inventors conducted further research based on this finding, and accomplished the present invention. Specifically, the present invention includes the following subject matter.

Item 1. A method for producing a perfluoroalkadiene compound represented by general formula (1):

$$CF_2=CF-(CF_2)_{n-4}-CF=CF_2 \quad (1)$$

wherein n is an integer of 4 or more,
the method comprising a reaction step of adding a nitrogen-containing compound to a solution of a compound represented by general formula (2):

$$X^1CF_2-CFX^2-(CF_2)_{n-4}-CF_2-CF_2X^1 \quad (2)$$

wherein n is the same as above, $X^1$ is the same or different and is a halogen atom other than fluorine, and $X^2$ is a halogen atom.

Item 2. The production method according to Item 1, wherein the nitrogen-containing compound has an addition rate of 0.001 to 60 mol/h per mol of the compound represented by general formula (2).

Item 3. The production method according to Item 1 or 2, wherein the nitrogen-containing compound is N,N-dimethylformamide.

Item 4. The production method according to any one of Items 1 to 3, wherein the solution is a solution of an organic solvent.

Item 5. The production method according to Item 4, wherein the boiling point of the organic solvent is lower than the boiling point of the nitrogen-containing compound.

Item 6. The production method according to any one of Items 1 to 5, wherein in the reaction step, the solution of the compound represented by general formula (2) further comprises zinc or a zinc alloy.

Item 7. The production method according to any one of Items 1 to 6, wherein the nitrogen-containing compound is added after the solution of the compound represented by general formula (2) is heated.

Item 8. The production method according to Item 7, wherein the heating is performed at reflux temperature.

Item 9. A perfluoroalkadiene composition comprising: a perfluoroalkadiene compound represented by general formula (1):

$$CF_2=CF-(CF_2)_{n-4}-CF=CF_2 \quad (1)$$

wherein n is an integer of 4 or more, and
at least one additional compound selected from fluorocarbon compounds (excluding the perfluoroalkadiene compound represented by general formula (1)) having one or more double bonds.

Item 10. The perfluoroalkadiene composition according to Item 9, wherein the amount of the additional compound is 0.1 to 45 mol % when the total amount of the perfluoroalkadiene composition is 100 mol %.

Item 11. The perfluoroalkadiene composition according to Item 9 or 10, wherein the additional compound is at least one member selected from the group consisting of fluorine-containing alkene compounds having 4 or more carbon atoms and fluorine-containing alkane compounds having 4 or more carbon atoms.

Item 12. The perfluoroalkadiene composition according to any one of Items 9 to 11, wherein the perfluoroalkadiene compound is hexafluorobutadiene.

Item 13. The perfluoroalkadiene composition according to any one of Items 9 to 12, wherein the additional compound is at least one member selected from the group consisting of octafluoro-1-butene, octafluoro-2-butene, heptafluoro-1-butene, and heptafluoro-2-butene.

Item 14. An etching gas, a refrigerant, a heat transfer medium, a foaming agent, or a resin monomer, each comprising the perfluoroalkadiene composition according to any one of Items 9 to 13.

Advantageous Effects of Invention

According to the present invention, a perfluoroalkadiene compound can be produced at a high yield.

DESCRIPTION OF EMBODIMENTS

In the present invention, the term "comprise/contain" encompasses the concepts of "comprise," "consist essentially of," and "consist of."

The perfluoroalkadiene compound production method of the present invention is a method for producing a perfluoroalkadiene compound represented by general formula (1):

$$CF_2=CF-(CF_2)_{n-4}-CF=CF_2 \quad (1)$$

wherein n is an integer of 4 or more, and the method comprises a reaction step of adding a nitrogen-containing compound to a solution of a compound represented by general formula (2):

$$X^1CF_2-CFX^2-(CF_2)_{n-4}-CF_2-CF_2X^1 \quad (2)$$

wherein n is the same as above, $X^1$ is the same or different and is a halogen atom other than fluorine, and $X^2$ is a halogen atom.

In general formulae (1) and (2), n is an integer of 4 or more, preferably 4 to 20, and more preferably 4 to 10. When n is in this range, the perfluoroalkadiene compound can be obtained at a higher yield.

Specifically, examples of the perfluoroalkadiene compound of general formula (1) to be produced include $CF_2=CF-CF=CF_2$, $CF_2=CF-CF_2-CF=CF_2$, $CF_2=CF-CF_2-CF_2-CF=CF_2$, etc.

In general formula (2), $X^1$ is a halogen atom other than fluorine, and examples include chlorine, bromine, iodine, etc. Of these, chlorine or iodine is preferred because the perfluoroalkadiene compound can be obtained at a higher yield. Each $X^1$ may be the same or different.

In general formula (2), $X^2$ is a halogen atom, and examples include fluorine, chlorine, bromine, iodine, etc. Of these, fluorine or chlorine is preferred, and chlorine is more preferred because the perfluoroalkadiene compound can be obtained at a higher yield.

Examples of the compound of general formula (2) that satisfy the above conditions include $ClCF_2-CFCl-CF_2-CF_2I$, $ClCF_2-CFCl-CF_2-CF_2-CF_2I$, $ClCF_2-CFCl-CF_2-CF_2-CF_2-CF_2I$, $ICF_2-CF_2-CF_2-CF_2I$, $ICF_2-CF_2-CF_2-CF_2-CF_2I$, $ICF_2-CF_2-CF_2-CF_2-CF_2-CF_2I$, etc. Because the perfluoroalkadiene compound can be obtained at a higher yield, $ClCF_2-CFCl-CF_2-CF_2I$, $ClCF_2-CFCl-CF_2-CF_2-CF_2I$, and $ClCF_2-CFCl-CF_2-CF_2-CF_2-CF_2I$ are preferred, and $ClCF_2-CFCl-CF_2-CF_2I$ is more preferred.

In the production method of the present invention, a solution of the compound represented by general formula (2) is first prepared. As an organic solvent used in the solution, a nonpolar organic solvent is preferred. Such an organic solvent preferably has a boiling point lower than that of a nitrogen-containing compound, because the nitrogen-containing compound is added after the solution of the compound represented by general formula (2) is heated. Examples of organic solvents include heptane, hexane, benzene, toluene, xylene, etc.

The amount of the organic solvent to be used is not limited, as long as it is a solvent amount; and is preferably 3 to 55 mol, and more preferably 4 to 8.5 mol, per mol of the compound represented by general formula (2).

The nitrogen-containing compound is not limited, as long as it is a compound containing nitrogen. Examples include amide compounds (such as N,N-dimethylformamide and N,N-diisopropylformamide), amine compounds (such as triethylamine), pyridine compounds (such as pyridine, methylpyridine, and N-methyl-2-pyrrolidone), quinoline compounds (such as quinoline and methylquinoline), etc. Such nitrogen-containing compounds can be used alone, or in a combination of two or more. Of these, amide compounds are preferred, and N,N-dimethylformamide is more preferred, because the perfluoroalkadiene compound can be obtained at a higher yield.

The nitrogen-containing compound may be a liquid at room temperature; however, the nitrogen-containing compound is preferably used (in a small amount) as an additive rather than a solvent, because the perfluoroalkadiene compound can be obtained at a higher yield. The amount of the nitrogen-containing compound to be used is preferably 0.25 to 2 mol, and more preferably 0.5 to 1 mol, per mol of the compound represented by general formula (2).

The nitrogen-containing compound is preferably added after the solution of the compound represented by general formula (2) is heated (hereinbelow, sometimes referred to as "added afterwards"). The heating conditions are not limited; 50 to 200° C. is preferred, and 100 to 150° C. is more preferred. In particular, heating at reflux temperature is most preferred.

When the nitrogen-containing compound is added after heating (in particular, heating at reflux temperature), the addition rate (dropwise addition rate) of the nitrogen-containing compound is preferably 0.001 to 60 mol/h, and more preferably 0.01 to 10 mol/h, because the perfluoroalkadiene compound represented by general formula (1) can be obtained at a higher yield.

In the present invention, the addition of zinc or a zinc alloy during the reaction is preferred. This allows the reaction to proceed more readily, and enables obtainment of the perfluoroalkadiene compound represented by general formula (1) at a higher yield. Zinc or a zinc alloy is preferably added before heating.

When a zinc alloy is used, examples of elements that can be contained therein include lead, cadmium, iron, etc. Commercially available zinc sometimes contains impurities, such as lead, cadmium, and iron. The present invention includes those containing such impurities.

The amount of zinc or zinc alloy to be used is preferably 1 to 10 mol, and more preferably 2 to 5 mol, per mol of the compound represented by general formula (2), because the perfluoroalkadiene compound represented by general formula (1) can be obtained at a higher yield.

Reaction conditions other than the heating temperature are not limited. For example, the reaction atmosphere is preferably an inert gas atmosphere (nitrogen gas atmosphere, argon gas atmosphere, etc.), and the reaction time is such that the reaction sufficiently proceeds. After the completion of the reaction, purification treatment is performed according to a known method to obtain the perfluoroalkadiene compound represented by general formula (1).

The perfluoroalkadiene compound represented by general formula (1) can thus be obtained; however, the perfluoroalkadiene compound can also be obtained in the form of a perfluoroalkadiene composition comprising the perfluoroalkadiene compound represented by general formula (1), and at least one additional compound selected from fluorocarbon compounds (excluding the perfluoroalkadiene compound represented by general formula (1)) having one or more double bonds. Examples of the fluorocarbon compounds include fluorocarbon compounds having one or more double bonds, and 4 or more carbon atoms. Specific examples include one or two or more compounds selected from fluorine-containing alkene compounds having 4 or more carbon atoms, and fluorine-containing alkane compounds having 4 or more carbon atoms. To obtain a perfluoroalkadiene compound (hexafluorobutadiene) represented by general formula (1) wherein n is 4, the fluorine-containing alkene compound can sometimes be obtained in the form of a composition (perfluoroalkadiene composition) containing hexafluorobutadiene and at least one fluorine-containing alkene compound selected from octafluoro-1-butene (e.g., $CF_2=CFCF_2CF_3$), octafluoro-2-butene (e.g., $CF_3CF=CFCF_3$), heptafluoro-1-butene (e.g., $CF_2=CFCF_2CF_2H$, $CF_2=CFCFHCF_3$), and heptafluoro-2-butene (e.g., $CF_3CF=CHCF_3$).

When a fluorine-containing alkane compound having 4 or more carbon atoms is contained in the perfluoroalkadiene composition of the present invention that is formed for when the perfluoroalkadiene compound represented by general formula (1) is obtained, $HCF_2CF_2CF_2CF_2H$, $HCF_2CFHCF_2CF_3$, $CF_3CFHCFHCF_3$, etc., can be used as the fluorine-containing alkane compound. Such additional compounds can be efficiently used for various purposes, including etching gases for forming state-of-the-art microstructures such as semiconductors and liquid crystals; refrigerants; heat transfer media; foaming agents; resin monomers; etc., in the same manner as hexafluorobutadiene.

In the perfluoroalkadiene composition of the present invention, the amount of the perfluoroalkadiene compound represented by general formula (1) is preferably 55 to 99.9 mol % (particularly 73 to 99.9 mol %), and the amount of the additional compound is preferably 0.1 to 45 mol % (particularly 0.1 to 27 mol %), when the total amount of the perfluoroalkadiene composition of the present invention is 100 mol %.

As in the case of the single use of the perfluoroalkadiene compound as described above, the perfluoroalkadiene composition of the present invention can be efficiently used for various purposes, including etching gases for forming state-of-the-art microstructures such as semiconductors and liquid crystals; refrigerants; heat transfer media; foaming agents; resin monomers; etc.

EXAMPLES

The features of the present invention are clarified with reference to the Examples shown below. The present invention is not limited to these Examples.

Example 1

An Eggplant flask equipped with a condenser, to which a trap is connected, was cooled to −78° C., and 40 g (0.16 mol) of xylene, 7.25 g (0.12 mol) of zinc, and 20 g (0.05 mol) of a starting material ($ClCF_2CFClCF_2CF_2I$) were added to the eggplant flask. Heating was then conducted under stirring until the inside temperature became 140° C. After the inside temperature became constant, N,N-dimethylformamide (DMF) was added dropwise under reflux at a dropwise addition rate of 0.04 mol/hour (0.8 mol/hour per mol of the starting material ($ClCF_2CFClCF_2CF_2I$)) for 1 hour, and heating reflux was continued while stirring. After the completion of the reaction, a liquid collected in the trap was analyzed by gas chromatography. The results showed that $CF_2=CFCF=CF_2$ was 89 mol %, $CF_2=CFCF_2CF_2H$ was 3 mol %, $HCF_2CF_2CF_2CF_2H$ was 0 mol %, and other side products (octafluoro-1-butene, octafluoro-2-butene, heptafluoro-1-butene other than $CF_2=CFCF_2CF_2H$, heptafluoro-2-butene, octafluorobutane other than $HCF_2CF_2CF_2CF_2H$) were 8 mol % in total. Specifically, the amount of the additional compounds was 11 mol %.

Example 2

Treatment was performed in the same manner as in Example 1, except that $ICF_2CF_2CF_2CF_2I$ was used as a starting material (substrate) in place of $ClCF_2CFClCF_2CF_2I$. After the completion of the reaction, a liquid collected in the trap was analyzed by gas chromatography. The results showed that $CF_2=CFCF=CF_2$ was 73 mol %, $CF_2=CFCF_2CF_2H$ was 20 mol %, $HCF_2CF_2CF_2CF_2H$ was 5 mol %, and other side products (octafluoro-1-butene, octafluoro-2-butene, heptafluoro-1-butene other than $CF_2=CFCF_2CF_2H$, heptafluoro-2-butene, octafluorobutane other than $HCF_2CF_2CF_2CF_2H$) was 2 mol %. Specifically, the amount of the additional compounds was 27 mol.

Reference Example 1

20 g (0.27 mol) of N,N-dimethylformamide (DMF) and 9 g (0.14 mol) of zinc were added to an eggplant flask equipped with a condenser that was cooled to −78° C., and to which a trap was connected. The flask was stirred and heated until the inside temperature became 140° C. After the inside temperature became constant, 20 g (0.04 mol) of a starting material ($ICF_2CF_2CF_2CF_2I$) was added thereto, and heating reflux was continued while stirring. After the completion of the reaction, a liquid collected in the trap was analyzed by gas chromatography. The results showed that $CF_2=CFCF=CF_2$ was 4 mol %, $CF_2=CFCF_2CF_2H$ was 11 mol %, $HCF_2CF_2CF_2CF_2H$ was 71 mol %, and other side products (octafluoro-1-butene, octafluoro-2-butene, heptafluoro-1-butene other than $CF_2=CFCF_2CF_2H$, heptafluoro-2-butene, octafluorobutane other than $HCF_2CF_2CF_2CF_2H$) were 14 mol %. Specifically, the amount of the additional compounds was 96 mol %.

Reference Example 2

Treatment was performed in the same manner as in Reference Example 1, except that $ClCF_2CFClCF_2CF_2I$ was used as a starting material (substrate) in place of $ICF_2CF_2CF_2CF_2I$. After the completion of the reaction, a liquid collected in the trap was analyzed by gas chromatography. The results showed that $CF_2=CFCF=CF_2$ was 42 mol %, $CF_2=CFCF_2CF_2H$ was 47 mol %, $HCF_2CF_2CF_2CF_2H$ was 0 mol %, and other side products (octafluoro-1-butene, octafluoro-2-butene, heptafluoro-1-butene other than $CF_2=CFCF_2CF_2H$, heptafluoro-2-butene, octafluorobutane other than $HCF_2CF_2CF_2CF_2H$) were 11 mol %. Specifically, the amount of the additional compounds was 58 mol %.

Reference Example 3

Treatment was performed in the same manner as in Reference Example 1, except that the mixed solvent of 20 g (0.19 mol) of xylene and 2.36 g (0.03 mol) of DMF was used in place of 20 g (0.27 mol) of DMF solvent. After the completion of the reaction, a liquid collected in the trap was analyzed by gas chromatography. The results showed that $CF_2=CFCF=CF_2$ was 55 mol %, $CF_2=CFCF_2CF_2H$ was 22 mol %, $HCF_2CF_2CF_2CF_2H$ was 13 mol %, and other side products (octafluoro-1-butene, octafluoro-2-butene, heptafluoro-1-butene other than $CF_2=CFCF_2CF_2H$, heptafluoro-2-butene, octafluorobutane other than $HCF_2CF_2CF_2CF_2H$) were 10 mol %. Specifically, the amount of the additional compounds was 45 mol %.

Reference Example 4

Treatment was performed in the same manner as in Reference Example 1, except that $ClCF_2CFClCF_2CF_2I$ was used as a starting material (substrate) in place of $ICF_2CF_2CF_2CF_2I$, and the mixed solvent of 20 g (0.19 mol) of xylene and 2.36 g (0.03 mol) of DMF was used in place of 20 g (0.27 mol) of DMF solvent. After the completion of the reaction, a liquid collected in the trap was analyzed by gas chromatography. The results showed that $CF_2=CFCF=CF_2$ was 48 mol %, $CF_2=CFCF_2CF_2H$ was 39 mol %, $HCF_2CF_2CF_2CF_2H$ was 0 mol %, and other side products (octafluoro-1-butene, octafluoro-2-butene, heptafluoro-1-butene other than $CF_2=CFCF_2CF_2H$, heptafluoro-2-butene, octafluorobutane other than $HCF_2CF_2CF_2CF_2H$) were 13 mol %. Specifically, the amount of the additional compounds was 52 mol %.

Table 1 shows the results.

Example 3

Under the etching conditions of 600 W of ICP (Inductive Coupled Plasma) discharge power, 200 W of bias power, 3 mTorr of pressure (0.399 Pa), $8\times10^{10}$ to $2\times10^{11}$ cm$^3$ of electron density, and 5 to 7 eV of electron temperature, a semiconductor substrate having an $SiO_2$ film with a thickness of about 1 μm on an Si substrate, and a resist pattern with a 0.21-μm-diameter hole formed thereon, was etched using cyclic $C_4F$ (conventional product) and $C_4F_6$ (structure: $CF_2=CFCF=CF_2$) containing the additional components produced in Example 1. Table 2 shows the etching rate and selectivity in the etching.

Both the resist selectivity for electron beam lithography and the silicone selectivity of $C_4F_6$ (structure: $CF_2=CFCF=CF_2$) were higher than those of c-$C_4F_8$.

TABLE 2

| Gas | $SiO_2$ etching rate Å/min | Resist etching rate Å/min | Resist selectivity $SiO_2$/Resist | Si etching rate Å/min | Silicone selectivity $SiO_2$/Si |
|---|---|---|---|---|---|
| c-$C_4F_8$ (Conventional product) | 6776 | 5061 | 1.34 | 2748 | 2.47 |
| $C_4F_6$ | 5470 | 2442 | 2.24 | 870 | 6.29 |

The invention claimed is:

1. A perfluoroalkadiene composition comprising:
   a perfluoroalkadiene compound represented by general formula (1):

$$CF_2=CF-(CF_2)_{n-4}-CF=CF_2 \quad (1)$$

wherein n is an integer of 4 or more, and
   a fluorine-containing alkene compound having 4 or more carbon atoms,
   wherein the amount of the fluorine-containing alkene compound is 0.1 to 3 mol % when the total amount of the perfluoroalkadiene composition is 100 mol %.

2. The perfluoroalkadiene composition according to claim 1, wherein the perfluoroalkadiene compound is hexafluorobutadiene.

3. The perfluoroalkadiene composition according to claim 1, wherein the fluorine-containing alkene compound is at least one member selected from the group consisting of octafluoro-1-butene, octafluoro-2-butene, heptafluoro-1-butene, and heptafluoro-2-butene.

4. The perfluoroalkadiene composition according to claim 2, wherein the fluorine-containing alkene compound is at least one member selected from the group consisting of octafluoro-1-butene, octafluoro-2-butene, heptafluoro-1-butene, and heptafluoro-2-butene.

5. An etching gas, a refrigerant, a heat transfer medium, a foaming agent, or a resin monomer, each comprising the perfluoroalkadiene composition according to claim 1.

6. An etching gas, a refrigerant, a heat transfer medium, a foaming agent, or a resin monomer, each comprising the perfluoroalkadiene composition according to claim 2.

7. An etching gas, a refrigerant, a heat transfer medium, a foaming agent, or a resin monomer, each comprising the perfluoroalkadiene composition according to claim 3.

TABLE 1

| | Example | | Reference Example | | | |
|---|---|---|---|---|---|---|
| | 1 | 2 | 1 | 2 | 3 | 4 |
| Substrate | $ClCF_2CFClCF_2CF_2I$ | $ICF_2CF_2CF_2CF_2I$ | $ICF_2CF_2CF_2CF_2I$ | $ClCF_2CFClCF_2CF_2I$ | $ICF_2CF_2CF_2CF_2I$ | $ClCF_2CFClCF_2CF_2I$ |
| Solvent | Xylene | Xylene | DMF | DMF | DMF + Xylene | DMF + Xylene |
| Additive | DMF added afterwards | DMF added afterwards | — | — | — | — |
| Generated gas purity (%) | | | | | | |
| $CF_2=CF-CF=CF_2$ | 89 | 73 | 4 | 42 | 55 | 48 |
| $CF_2=CFCF_2CF_2H$ | 3 | 20 | 11 | 47 | 22 | 39 |
| $HCF_2CF_2CF_2CF_2H$ | 0 | 5 | 71 | 0 | 13 | 0 |
| Others | 8 | 2 | 14 | 11 | 10 | 13 |

8. An etching gas, a refrigerant, a heat transfer medium, a foaming agent, or a resin monomer, each comprising the perfluoroalkadiene composition according to claim 4.

* * * * *